(12) United States Patent
Tanaka et al.

(10) Patent No.: US 7,209,614 B2
(45) Date of Patent: Apr. 24, 2007

(54) OPTICAL FIBER TAPE OF LOW POLARIZATION MODE DISPERSION CHARACTERISTIC AND METHOD FOR MEASURING DYNAMIC VISCOELASTICITY OF THE OPTICAL FIBER TAPE

(75) Inventors: Hiroki Tanaka, Tokyo (JP); Yasuo Nakajima, Tokyo (JP); Mitsunori Okada, Tokyo (JP); Norimitsu Takaishi, Tokyo (JP); Kenichi Mizoguchi, Tokyo (JP); Hidetoshi Yasui, Tokyo (JP)

(73) Assignee: The Furukawa Electric Co., Ltd., Tokyo (JP)

( * ) Notice: Subject to any disclaimer, the term of this patent is extended or adjusted under 35 U.S.C. 154(b) by 0 days.

(21) Appl. No.: 11/075,877

(22) Filed: Mar. 10, 2005

(65) Prior Publication Data

US 2005/0244117 A1    Nov. 3, 2005

Related U.S. Application Data

(63) Continuation of application No. PCT/JP03/11579, filed on Sep. 10, 2003.

(30) Foreign Application Priority Data

Sep. 11, 2002 (JP) .............................. 2002-265366

(51) Int. Cl.
*G02B 6/44* (2006.01)
(52) U.S. Cl. .................... 385/114; 385/128; 385/141
(58) Field of Classification Search ..................... None
See application file for complete search history.

(56) References Cited

U.S. PATENT DOCUMENTS

| | | | | |
|---|---|---|---|---|
| 4,875,758 A | | 10/1989 | Masuda et al. | |
| 5,402,516 A | * | 3/1995 | Blyler et al. | 385/141 |
| 5,845,032 A | * | 12/1998 | Konda et al. | 385/110 |
| 5,905,838 A | * | 5/1999 | Judy et al. | 385/123 |
| 6,160,940 A | | 12/2000 | Summers et al. | |
| 2004/0022510 A1 | * | 2/2004 | Suzuki et al. | 385/128 |
| 2004/0213531 A1 | * | 10/2004 | Sasaoka | 385/123 |
| 2005/0226573 A1 | * | 10/2005 | Okuno et al. | 385/114 |

FOREIGN PATENT DOCUMENTS

| | | |
|---|---|---|
| EP | 0 323 635 A2 | 7/1989 |
| EP | 0 938 001 A1 | 8/1999 |
| JP | 2-20812 | 1/1990 |
| JP | 7-318770 | 12/1995 |

(Continued)

*Primary Examiner*—Frank G. Font
*Assistant Examiner*—Eric Wong
(74) *Attorney, Agent, or Firm*—Oblon, Spivak, McClelland, Maier & Neustadt, P.C.

(57) ABSTRACT

An optical fiber tape having low polarization mode dispersion characteristics and applied to a dense wavelength multiplex (DWDM) transmission system of a transmission rate from several Gb/s to several tens of Gb/S. We have found out that the polarization mode dispersion of an optical fiber tape relates to the loss tangent (tan $\delta$) determined when the dynamic viscoelasticity is measured, and that particularly, if the loss tangent of when a dispersion shift fiber is used is made 0.080 or more and the loss tangent of when a single mode optical fiber is used is made 0.042 or more, the polarization mode coefficient of dispersion (PMD) is reduced to 0.3 ps/$\sqrt{km}$ preferable to realize a DWDM transmission system.

12 Claims, 7 Drawing Sheets

FOREIGN PATENT DOCUMENTS

| | | |
|---|---|---|
| JP | 8-43694 | 2/1996 |
| JP | 8-146260 | 6/1996 |
| JP | 10-206708 | 8/1998 |
| JP | 11-281840 | 10/1999 |
| JP | 2000-121893 | 4/2000 |
| JP | 2000-145970 | 5/2000 |
| JP | 2000-155248 | 6/2000 |

* cited by examiner

DMS16

- DISPERSION SHIFT FIBER
- SINGLE MODE OPTICAL FIBER

OPTICAL FIBER TAPE OF LOW POLARIZATION MODE DISPERSION CHARACTERISTIC AND METHOD FOR MEASURING DYNAMIC VISCOELASTICITY OF THE OPTICAL FIBER TAPE

TECHNICAL FIELD

The present invention relates to an optical fiber tape composed of a plurality of optical fibers integrated into a tape form. More particularly, the invention relates to an optical fiber tape for use in high speed transmission, ranging in transmission speed from several Gb/s to several tans of Gb/s.

BACKGROUND ART

Along with the rapidly spreading use of the Internet and the expansion of business communication networks, the demand for communication is dramatically increasing with the consequence that the capacities of relayed networks are falling short of the requirement. In this connection, optical fiber networks are pressed for further increases in speed and capacity.

A transmission technique known as dense wavelength division multiplex (hereinafter abbreviated to DWDM), which allows an optical fiber to propagate many wavelengths, is attracting note and coming into growing use as a technique that makes possible a big leap in the expansion of transmission capacities for relay networks owned by communications operators especially in urban areas.

The DWDM transmission technique allows transmission of a plurality of optical signals differing in wavelength over a single optical fiber; it is a technique that makes possible a big leap in the expansion of transmission capacity of a single optical fiber. Particularly in next-generation large capacity and high speed systems for transmission at such a high speed as 10 Gb/s or even 40 Gb/s, the influence of polarization mode dispersion (hereinafter abbreviated to PMD) is at work in addition to usual dispersion characteristics, inviting a further increase in coefficient s contributing to waveform deterioration during transmission. For this reason, the problem of how to reduce this polarization mode dispersion has come to take on extreme importance.

Polarization mode dispersion is a phenomenon that occurs when an optical wave comes incident between one optical axes {a fast direction (y-polarized) or a slow direction (x-polarized)} and another (e.g. at 45°), equivalent to each other generated by the birefringence within the optical fiber, a difference in refractive index between two mutually orthogonal polarized components gives rise to a difference in group delay time between the two polarizations and thereby widens the optical pulse. The magnitude of polarization mode dispersion is represented by the difference in group delay time in the lengthwise direction of the orthogonal polarization arising from the elliptical deformation of the core and traces of anisotropic stresses (including those due to lateral pressure, bending, torsion, tension and thermal stress due to temperature variation), and this difference in group delay time is defined as PMD (unit: ps) by the International Telecommunication Union (abbreviated to ITU).

The quotient of the division of that polarization mode dispersion by the square root of the distance is defined to be the polarization mode dispersion (PMD) coefficient (unit: ps/$\sqrt{km}$). This difference in group delay time is also referred to as DGD (differential group delay; unit: ps).

Whereas optical fibers should be spliced to each other in architecting a communication system, there are a few kinds of splicing methods for that purpose The fusion splicing method, which excels in reliability and connecting performance among them, has a disadvantage of taking a longer time per splice than other methods. What has been developed to increase the density of and reducing the length of time taken to fusion-splice these cables is the optical fibertape. For instance in J. Kohtala, J. Tanskanen, P. Fickling, and M. Eriksson, "A High Speed Coating Process for Optical Fiber Ribbon", in *Proceedings of International Wire Cable Symposin.* '91 (St. Louis, U.S.A.), 1991, pp. 550–555", its structure and fabrication method are described.

In the general structure of an optical fiber tape optical fiber are arranged in a lateral row and integrated. For example, an optical fiber consists of an optical fiber glass as such measuring 125 μm in diameter coated by a covering layer and a coloring layer of a few μm to make the external diameter 250 μm. Available optical fiber include quartz-based single-mode optical fibers, quartz-based multi-mode optical fibers and dispersion shift optical fibers, basically composed of silica glass or germanium doped glass.

Two methods are available for integration, one of adhering adjoining optical fibers and the other of cladding adjoining optical fibers with a tape layer. The number of optical fibers accommodated in a single optical fiber tape is prescribed to be 2, 4, 5, 6, 8, 10 or 12 according to JISC 6838.

Many such optical fiber tapes are put together into a cable form to configure an optical fiber cable. The advancement of optical amplification techniques in recent years has made possible non-regenerative relay transmission for hundreds to thousands of kilometers by using a single mode optical fiber or a dispersion shift optical fiber.

However, since the deterioration of optical signals by polarization mode dispersion poses a problem in such long distance transmission, especially in a DWDM transmission system, realization of optical fiber cables susceptible to little polarization mode dispersion is in keen demand. In order to achieve optically amplified transmission over a long distance of hundreds to thousands of kilometers at a transmission speed of several Gb/s to several tens of Gb/s, the polarization mode dispersion coefficient of the optical fiber cable should be kept at no more than 0.3 ps/$\sqrt{km}$, more preferably at no more than 0.2 ps/$\sqrt{km}$.

For these reasons, optical fiber tapes are also required to have superior PMD characteristics. However, there is a problem that, even if optical fibers themselves are superior in polarization mode dispersion, their integration into a tape invites deterioration in polarization mode dispersion. Also, whereas a tape-shaped optical fiber usually accommodates a plurality of optical fibers, there is a further problem of differences in PMD characteristics among the individual optical fibers. Thus, in the prevailing state, the polarization mode dispersion of optical fiber tapes has been inadequate especially for use in a DWDM system for long distance transmission.

The present invention is intended to provide an optical fiber tape core adaptable to transmission at high speed of 10 Gb/s or even 40 Gb/s.

SUMMARY OF THE INVENTION

The present invention is to provide a manufacturing method and a designing method for optical fiber tapes, characterized in that they include a step of figuring out the polarization mode dispersion counts of optical fibers in the optical fiber tape from the loss tangent of the optical fiber tape.

An optical fiber tape according to the invention integrates a plurality of optical fibers with a tape bonding material, and is characterized in that the maximum level of the polarization mode dispersion of any optical fiber in the optical fiber tape is not more than 0.3 ps/$\sqrt{km}$. In particular, it is an optical fiber tape composed by arranging a plurality of resin-coated optical fiber in one lateral row and then using an ultraviolet curing resin around the optical fibers as the tape bonding material, characterized in that the maximum level of the polarization mode dispersion of any optical fiber in the optical fiber tape is not more than 0.3 ps/$\sqrt{km}$, more preferably 0.2 ps/$\sqrt{km}$.

These optical fiber tapes can be realized by setting the local maximum level of the loss tangent at or more than 0.080, more preferably at or more than 0.085, or at or more than 0.042, more preferably at or more than 0.050. In particular, where dispersion shift fibers are used as the optical fibers, it is appropriate to set the local maximum level of the loss tangent at or more than 0.080 or, where single mode optical fibers are used as optical fibers, to set the local maximum level of the loss tangent at or more than 0.042.

The present invention provides a method of measuring the dynamic viscoelasticity of optical fiber tapes after ultraviolet curing, characterized in that a stress is applied in the axial direction of optical fibers in a state in which optical fibers remain within and a method optical of manufacturing fiber tapes including that measuring method.

The invention provides a slot type optical fiber cable characterized in that the optical fiber tapes is accommodated in a slot of a slotted spacer. One example of that slot type optical fiber cable is a slot type optical fiber cable the spacer of which is a spacer having an SZ spiral type slot whose spiraling direction is periodically reversed.

One example of tape bonding material is an ultraviolet curing resin, and this ultraviolet curing resin consists of photopolymerizing prepolymer,
photopolymerizing monomer
or
photopolymerization initiator.

To add, it is appropriate to select as the tape bonding material a resin whose loss tangent is not less than 0.60.

For the optical fiber tape according to the invention, the tape bonding material is so prescribed that the polarization mode dispersion coefficient count of each of the plurality of optical fibers be not more than 0.3 ps/$\sqrt{km}$.

In one example of configuration of the optical fiber tape according to the invention, it is a capsulate structure in which the tape bonding material wholly coats the plurality of optical fibers.

A dense wavelength division multiplex (DWDM) system according to the invention comprises a first optical multiplexer/demultiplexer for a plurality of optical signals, a first optical multiplexer/demultiplexer for a plurality of optical signals, and the optical fiber tape arranged between the first and second optical multiplexer/demultiplexers or an optical fiber cable accommodating that optical fiber tape, wherein the signal transmission speed on that transmission path ranges from several Gb/s to several tens of Gb/s.

PREFERRED EMBODIMENTS

Figure 1:
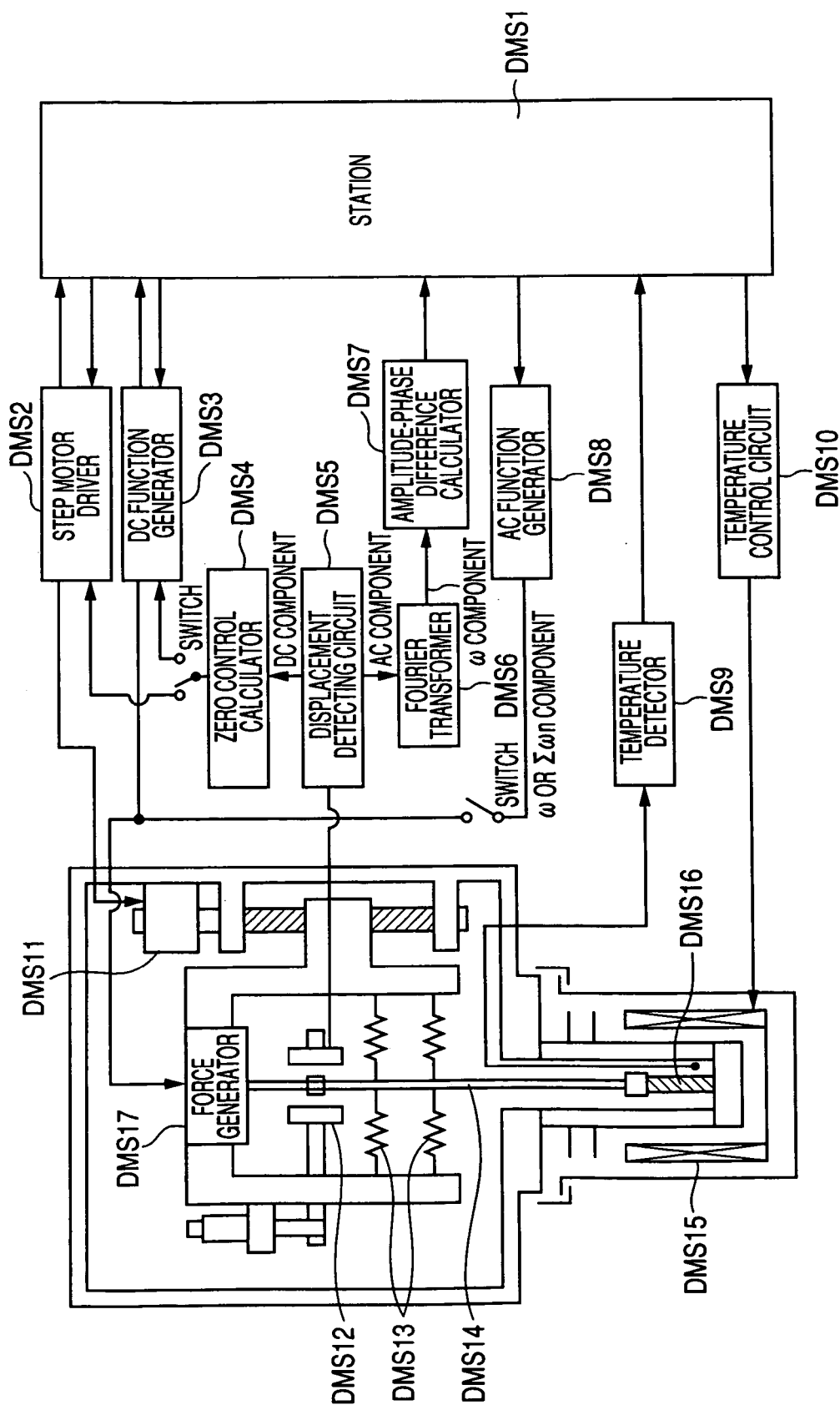
FIG. 1 is a schematic diagram of a tensile type dynamic viscoelasticity measuring system.

We took note, as one of the factors affecting the polarization mode dispersion of optical fiber tapes, of the material of the tape covering layer, and studied it thoroughly. As a result, it was found that the loss tangent (tan δ), which was figured out in the measurement of the dynamic viscoelasticity of an optical fiber tape, measured in a state in which a stress was applied in the axial direction of the optical fiber where the optical fiber was in the optical fiber tape, was relevant to the PMD coefficient; in particular we found that, by setting the loss tangent at. 0.080 or more where a dispersion shift fiber was used and setting the loss tangent at 0.042 or more where a single mode optical fiber was used, the PMD coefficient of each optical fiber could be kept at 0.3 ps/$\sqrt{km}$ or less. It turned out that, more preferably by setting the loss tangent at 0.085 or more where a dispersion shift fiber was used and setting the loss tangent at 0.050 ore more where a single mode optical fiber was used, the PMD coefficient could be kept at 0.2 ps/$\sqrt{km}$ or less.

As the tape bonding material, an ultraviolet-curing resin was used, for instance; examples of such ultraviolet curing resins include
photopolymerizing prepolymers,
photopolymerizing monomers
and photopolymerization initiators; and the
photopolymerizing prepolymers
include urethane
acrylate resins,
epoxy acrylate resins,
polyol acrylate resins,
butadiene acrylate resins,
polyester acrylate resins,
silicon acrylate resins.

The photopolymerizing monomers include
vinyl pyrrolidones, hydroxy ethyl acrylates,
ethylhexyl acrylates.

Further, the photopolymerization initiators include benzophenone compounds,
acryl phosphine oxide compounds
and acetophenone compounds.

(Method of Measuring Loss Tangent)

Dynamic viscoelasticity is the viscoelasticity that is observed when a periodically varying distortion or stress is applied to an object. By measuring dynamic viscoelasticity, data on the storage modulus (G'), loss modulus (G") and loss tangent (tan δ=G"/G') can be obtained. The storage modulus represents the elastic element of a substance, the loss modulus represent the viscous element of a substance, and the loss tangent, the quotient of division of the loss modulus by the storage modulus, represents the balance between the elastic element and the viscous element. In a fully elastic object, the stress is proportional to the distortion, and the stress (phase difference zero) is detected without delay for any given stress. In a fully viscous object, on the other hand, as the stress is proportional to the velocity of distortion, when a stress is given at sin (ωt), the distortion of response is −cos(ωt)=sin(ωt−π/2)1; thus the distortion is detected ¼ wavelength (phase difference: π/2) behind the stress.

In this measurement, the phase difference is figured out by detecting the displacement quantity of a sample when subjected to an alternating current. force, and performing Fourier operation from the A.C. force applied to the sample and the detected displacement quantity. A typical high molecule is positioned between a fully elastic object and viscous object, and its phase difference ranges between 0 and π/2. The relationship between stress and distortion is measured to output a loss tangent which represents the ratio between the storage modulus of the elastic component and the loss modulus of the viscous component, which are dynamical characteristics.

The loss tangent in the dynamic viscoelasticity of an optical fiber tape was figured out by using a tensile type dynamic viscoelasticity apparatus shown in FIG. 1. At an instruction from a station DMS1, an AC function generator applies an AC signal to a force generator DMS17. The force generator DMS17 drives with an AC a probe DMS14 to which a compliance is given by a leaf spring DMS13. The probe applies a tensile stress to a sample DMS16 installed on a jig. The viscoelasticity of the sample then is detected by a differential trans-sensor DMS12 as a displacement, whose AC component is analyzed as a detection signal by a Fourier displacement detector DMS6 and an amplitude-phase difference calculator DMS7 via a displacement detecting circuit DMS5, and the analysis signal is sent to the station DKS1 to obtain the storage modulus (G'), loss modulus (G") and loss tangent (tan δ=G"/G'). The DC component of the displacement signal is delivered to a zero control calculator DMS4, which sets the zero position by controlling a stepping motor DMS11 via a stepping data driver DMS2. Its DC output is superposed over the AC force drive signal via a DC function generator DMS3. The sample DMS16 is given a sample temperature by a heater DMS15 controlled by a temperature detector DMS9 and a temperature control circuit DMS10.

Figure 2:
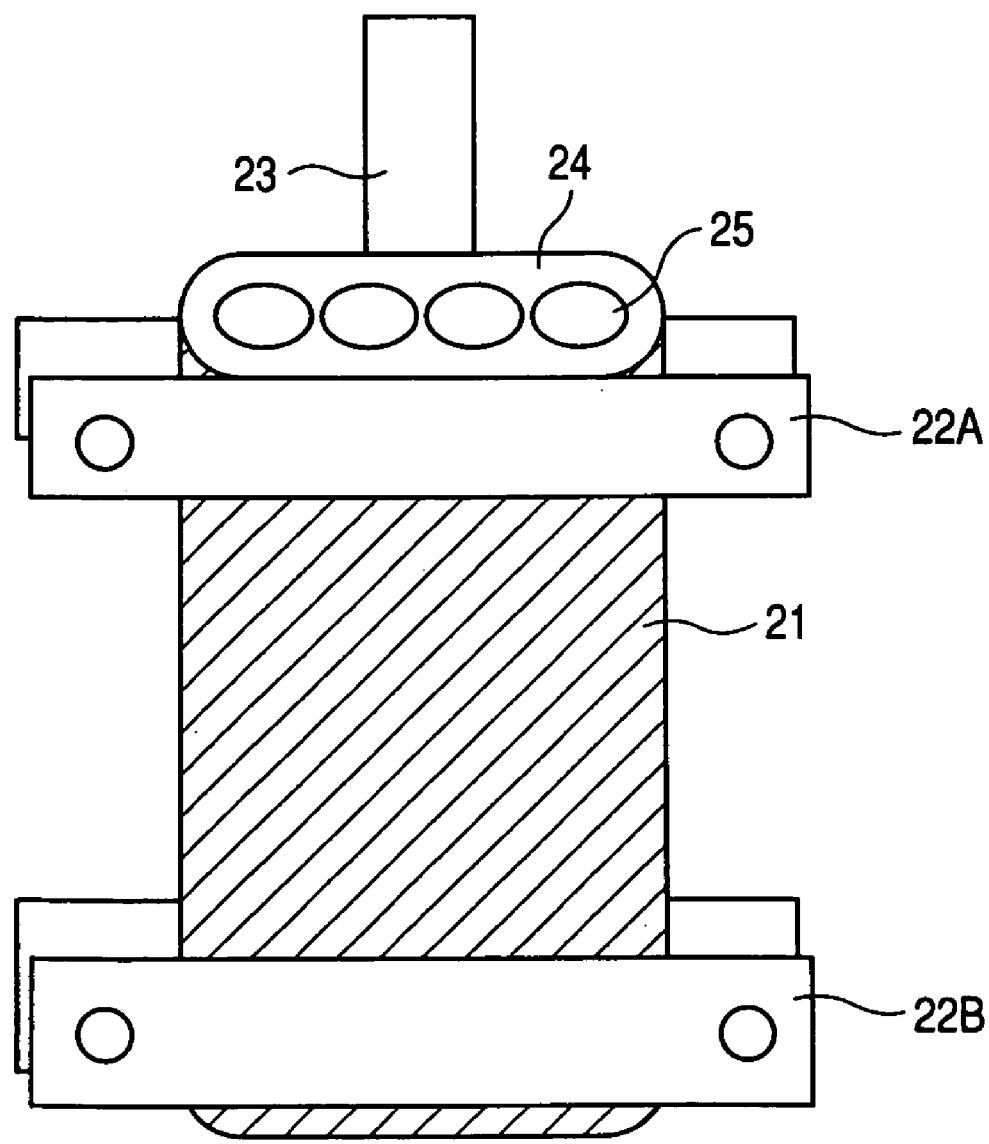
FIG. 2 is a diagram showing a measuring jig for optical fiber tape samples according to the invention.

FIG. 2 shows a jig to be applied to the tensile type dynamic viscoelasticity apparatus. The two ends of an optical fiber tape core sample 21, consisting of a tape bonding material 24 and optical fiber strands 25 and cut to an appropriate length, are fixed with fixing members 22A and 22B, and a tensile probe 23 linked to the fixing members apply an AC force of a prescribed frequency to the sample 21 in the direction of its longer axis. With the optical fiber tape sample being fixed in a state in which optical fiber remain therein as shown in FIG. 2, a stress was applied in the axial direction of the optical fiber to measure its viscoelasticity.

The loss tangent was thus figured by measuring the viscoelasticity of the optical fiber tape in the state in which optical fiber remain therein and, as a result, it was found to have a high correlation coefficient with the polarization mode dispersion coefficient of the optical fiber tape core.

(Method of Measuring PMD Coefficient)

The polarization mode dispersion was measured by the Jones matrix (JME) method. Regarding the measurement of polarization mode dispersion, a measuring method is described in, for instance, Yoshinori Namihira, *OPTRONICS* (2000) No. 8, pp. 146–157.

In the following specific example, the loss tangent was measured by the system, shown in FIG. 1 by using DMS 6100 (™) manufactured by Seiko Instruments Inc. as the dynamic viscoelasticity apparatus, with an optical fiber tape cut to a length of about 20 mm and fixed with a tensile type jig like the one shown in FIG. 2. Since dynamic viscoelasticity is dependent on the temperature of the optical fiber tape structure, the sample temperature was varied and measurement was done at different temperatures. The conditions of measurement were as follows.

Figure 3:
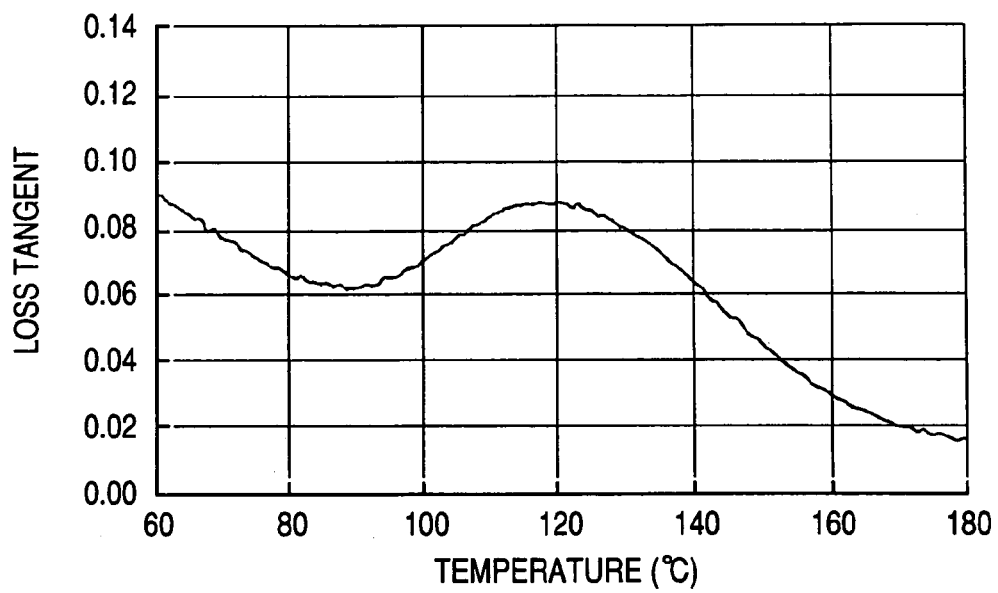
FIG. 3 is a diagram illustrating an example of measurement result of the dynamic viscoelasticity of optical fiber tapes.

Oscillation frequency of AC force: 33 Hz
Rising rate of sample temperature: 2° C./min One example of measurement done under the conditions is shown in FIG. 3. It is seen that the peak (the local maximum level) of the loss tangent appears in the temperature range of 80 to 150° C. The loss tangent at this local maximum level was figured out.

Regarding the ultraviolet curing resin itself, which is used as the tape bonding material. a film sample of 20 mm in length containing no fiber strand was prepared, and the highest level of the loss tangent and the temperature at this highest level were figured out by similarly measuring its dynamic viscoelasticity under the following conditions.

Figure 4:
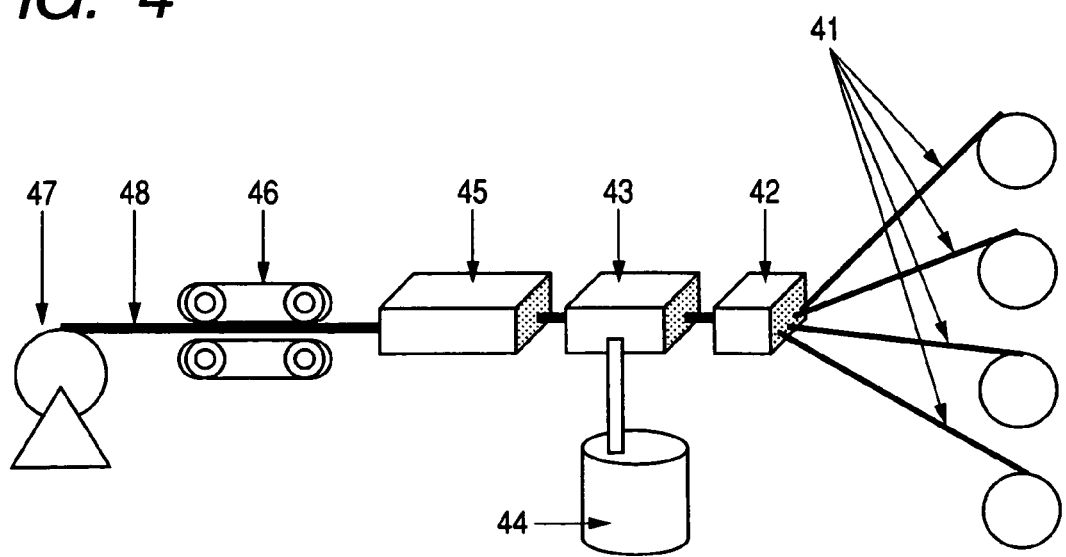
FIG. 4 is a schematic structural diagram of a manufacturing apparatus for optical fiber tapes according to the invention.

Oscillation frequency of AC force: 33 Hz
Rising rate of sample temperature: 2° C./min FIG. 4 is a schematic structural diagram of a manufacturing apparatus for four optical fibers tape according to the invention. Four optical fibers 41 were arranged one lateral row with an optical fiber assembling die 42, and the ultraviolet curing resin, which is the material of the tape bonding material, is fed from a feeder 44 to an optical fiber die 43, and the four optical fibers 41 were integrated to be coated with the ultraviolet curing resin in a tape form, followed by the hardening of the resin in an ultraviolet curing furnace 45. A completed optical fiber tape 48 is taken up around a take-up bobbin 47 via a belt capstan 46. Four optical fibers of 255 μm in external diameter were arranged in one lateral row by using this apparatus, and optical fiber tape of a capsulate structure of 1.12 mm in width and 0.33 mm in height shown in FIG. 5 were manufactured by coating them with ultraviolet curing resin for tape bonding use and then subjecting them to ultraviolet curing. The polarization mode dispersion of the optical fibers were measured by the Jones matrix method. What presented the highest polarization mode dispersion (PMD) coefficient out of the four fibers (i.e. the PMD coefficient count of the fiber having the highest PMD coefficient out of the plurality of accommodated fibers) was selected as the polarization mode dispersion coefficient count of this optical fiber tape.

Figure 5:
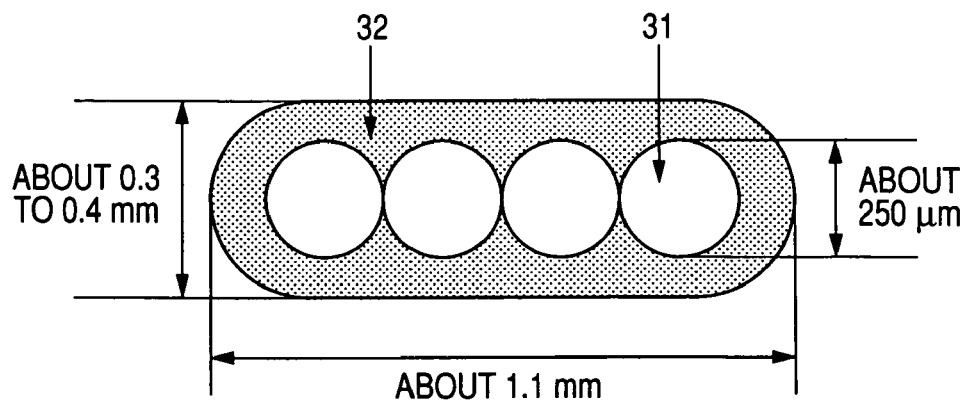
FIG. 5 is a diagram illustrating an example of capsulate structure of an optical fiber tape.

Eight kinds of optical fiber tapes of the configuration shown in FIG. 5, Example 1 through Example 8, were prepared, and the local maximum levels of the loss tangent and of the polarization mode dispersion were determined by the method described above. The optical fiber tapes of Example 1 through Example 8 were prepared by joining dispersion shift optical fibers or single mode optical fibers into a tape form with ultraviolet curing resins A through G as tape bonding materials. Regarding the ultraviolet curing resins A through G, the highest level of the loss tangent and the temperature at this highest level were also measured as film samples of 20 mm in length as described above. In measuring the film samples, films of 200 μm in thickness were prepared by irradiation with ultraviolet rays of 200 mW/cm$^2$ and 500 mJ/cm$^2$ in a nitrogen ambience, and the dynamic viscoelasticity of each was measured by the above-described method of dynamic viscoelasticity measurement, the loss tangent being figured out on that basis.

EXAMPLE 1

This is an optical fiber tape using resin A as the tape bonding material and dispersion shift optical fibers as the optical fibers.

EXAMPLE 2

This is an optical fiber tape using resin B as the tape bonding material and dispersion shift optical fibers as the optical fibers.

EXAMPLE 3

This is an optical fiber tape using resin C as the tape bonding material and dispersion shift optical fibers as the optical fibers.

EXAMPLE 4

This is an optical fiber tape using resin D as the tape bonding material and dispersion shift optical fibers as the optical fibers.

EXAMPLE 5

This is an optical fiber tape resin E as the tape bonding material and dispersion shift optical fiber as the optical fibers.

EXAMPLE 6

This is an optical fiber tape using resin B as the tape bonding material and single mode optical fibers as the optical fibers.

EXAMPLE 7

This is an optical fiber tape using resin F as the tape bonding material and single mode optical fibers as the optical fibers.

EXAMPLE 8

This is an optical fiber tape using resin G as the tape bonding material and single mode optical fibers as the optical fibers.

Figure 7:
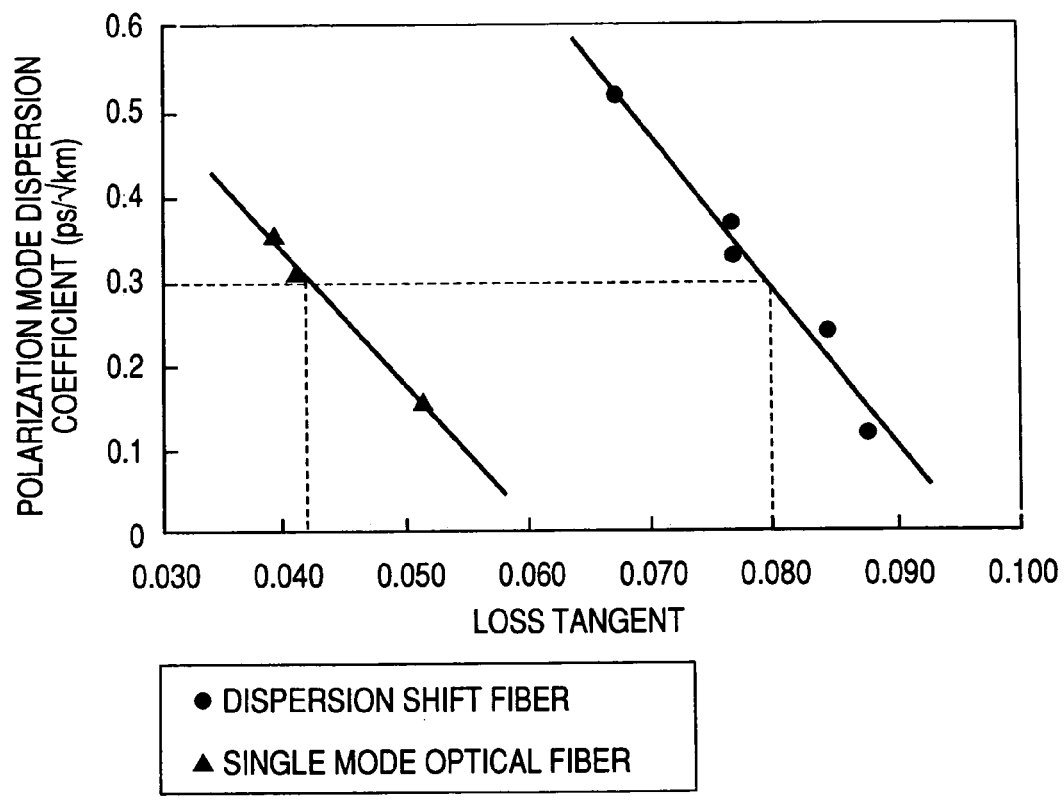
FIG. 7 is a diagram illustrating the polarization mode dispersion coefficient and the loss tangent of an optical fiber tape according to the invention.

The results of the foregoing are put together in Table 1, and the relationship between the polarization mode dispersion coefficient and the loss tangent of the optical fiber tape is shown in FIG. 7 in a graph form.

TABLE 1

|  | Example 1 | Example 2 | Example 3 | Example 4 | Example 5 | Example 6 | Example 7 | Example 8 |
| --- | --- | --- | --- | --- | --- | --- | --- | --- |
| Ultraviolet curing resin for tape layer | Resin A | Resin B | Resin C | Resin D | Resin E | Resin B | Resin F | Resin G |
| highest loss tangent of ultraviolet curing resin for tape layer | 0.60 | 0.71 | 0.48 | 0.55 | 0.56 | 0.71 | 0.62 | 0.64 |
| Temperature (° C.) when highest loss tangent of ultraviolet curing resin for tape layer is reached | 100 | 92 | 94 | 91 | 98 | 92 | 92 | 98 |
| Fiber type* | DS | DS | DS | DS | DS | SM | SM | SM |
| Loss tangent measured of optical fiber tape** | 0.085 | 0.088 | 0.077 | 0.068 | 0.077 | 0.051 | 0.039 | 0.041 |
| Polarization mode dispersion coefficient (ps/√km)*** | 0.24 | 0.12 | 0.33 | 0.52 | 0.37 | 0.16 | 0.36 | 0.32 |

*DS: Dispersion shift optical fiber; SM: Single mode optical fiber
**local Maximum level of loss tangent obtained at a temperature of 80° C. or above
***the highest level among four optical fibers As is seen from FIG. 7, the loss tangent at which the polarization mode dispersion coefficient is 0.3 ps/√km or less is 0.080 or more where a dispersion shift fiber is used or 0.042 or more where a single mode optical fibers are used. In the configurations of Example 1, Example 2 and Example 6 using Resins A and B, desired polarization mode dispersion coefficients were obtained. Thus, Examples 1, 2 and 6 pertain to the embodiment of the present invention, while Examples 3, 4, 5 and 7 are comparative examples. Raising the loss tangent of the tape covering material itself is also effective for reducing the polarization mode dispersion coefficient, and a choice of this coefficient at 0.60 or more also tends to give a desired polarization mode dispersion coefficient of 0.3 ps/√km or more. Resins A and B of Examples 1, 2 and 6 pertain to the embodiment of the invention are different from Resins C, D, E, F and G of Comparative Examples 3, 4 and 5.

Figure 12:
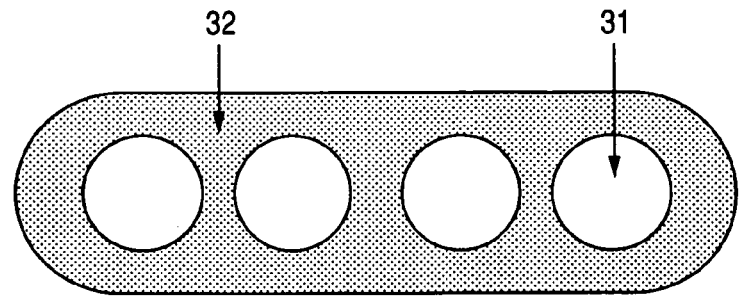
FIG. 12 is a diagram showing an example of capsulate structure of an optical fiber tape.

Incidentally, where the circumference of the four optical fibers are to be configured in a capsulate form coated with a lap bonding material according to the invention as shown in FIG. 5, though its dimensions usually form to JIS, i.e. 0.25±0.08 to 0.40±0.08 mm in tape thickness and 1.01±0.12 in tape width, these dimensions can be altered as appropriate where, for instance, thin optical fibers of 165 µm in diameter are to be used, the number of fiber is not four, or the available accommodating space so requires. Also, the gaps between the optical fibers may either be almost zero (FIG. 5) or slightly wider (FIG. 12).

Figure 6A:
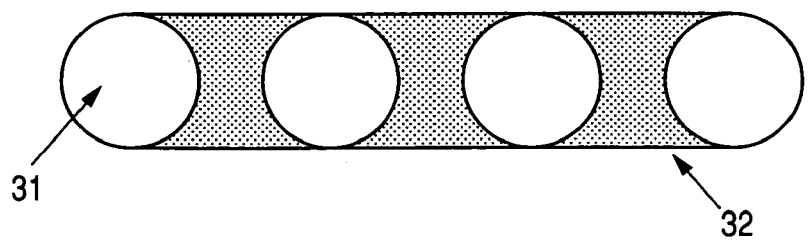
FIG. 6A is a diagram illustrating an example of edge-bonded structure of an optical fiber tape.
Figure 6B:
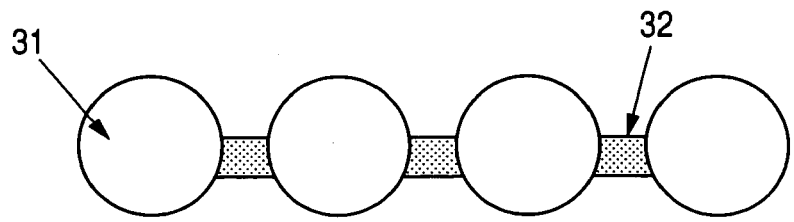
FIG. 6B is a diagram illustrating another example of edge-bonded structure of an optical fiber tape.

Apart from the capsulate form in which the circumference of the four optical fibers coated with a lap bonding material according to the invention as shown in FIG. 5, the invention can also be applied to the types of optical fiber tape structures shown in FIG. 6A and FIG. 6B. In the structures shown in FIG. 6A and FIG. 6B, adjoining optical fibers are bonded with a tape bonding material.

Figure 8:
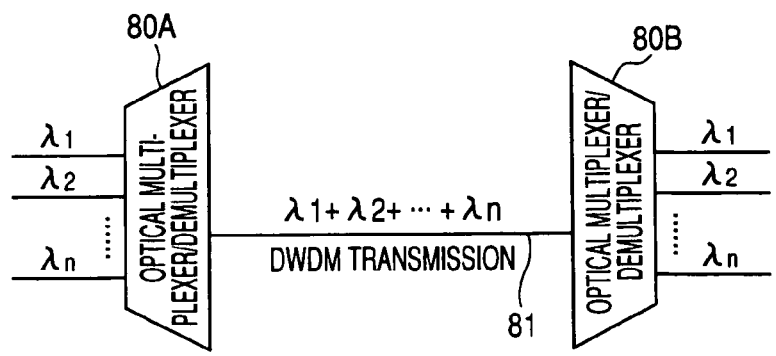
FIG. 8 is a diagram illustrating a DWDM system according to the invention.

FIG. 8 illustrates a DWDM system configuration according to the invention, in which an optical fiber cable transmission line 81 accommodating an optical fiber tape is arranged between optical multiplexer/demultiplexers 80A and 80B. Optical signals λ1, λ2 . . . λ2 are multiplexed on the transmission line 81, and information pulses are transmitted at a transmission speed of several Gb/s to several tens of Gb/s (e.g. 10 Gb/s or 40 Gb/s).

Figure 9:
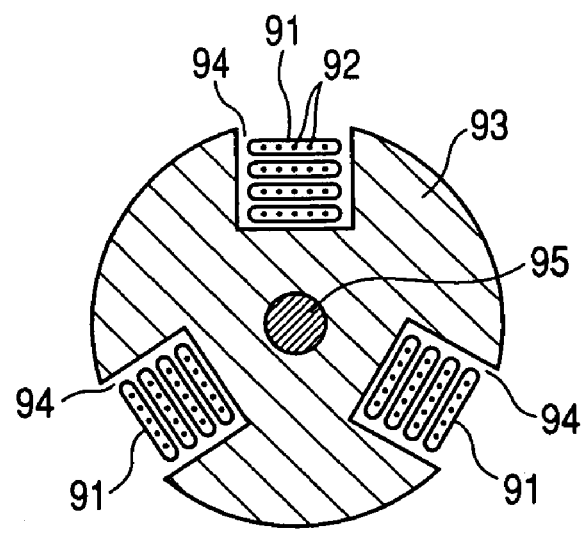
FIG. 9 is a diagram illustrating a slot type optical fiber cable accommodating an optical fiber tape according to the invention.
Figure 10:
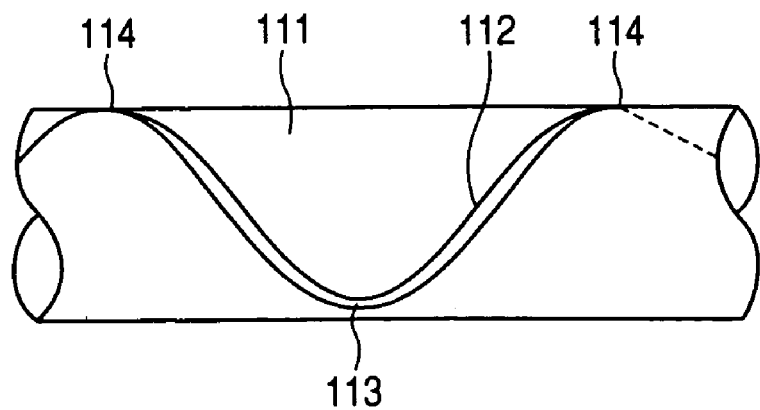
FIG. 10 is a diagram illustrating an SZ spiral type slot type optical fiber cable accommodating optical fiber tapes according to the invention.

The cable structure arranged as an example of transmission line of FIG. 8 accommodates the above-described optical fiber tape pertaining to the invention. An example of slot type optical cable is shown in FIG. 9. A plurality of slots 94 are formed in the outer circumference of a spacer 93 consisting of a resin or the like. In each of these slots 94, a plurality of stacked flat sheets of optical fibers pertaining to the invention are accommodated. Reference numeral 91 denotes optical fibers, and 95, a tension member consisting of a copper wire for instance. The structure of such a slot type optical cable itself is disclosed in, for instance, Japanese Patent Application Laid-Open No. 2-282709. In one of possible embodiments, the plurality of slots 94 in the outer circumference of this spacer 93 are SZ-spirally shaped. The optical fiber tape pertaining to the invention is accommodated in this spiral slots. And these spiral slots are so shaped that the spiraling direction is periodically reversed. Whereas a cable of such a configuration is shown in FIG. 10, this SZ slot type configuration itself is disclosed in, for instance, Japanese Patent Application Laid-Open No. 2-282709. A spiral groove 113 is formed in the outer circumference of a spacer 111, and a point 113 of the slot 112 is a reversing part of the spiraling direction, and a point 114 is the center of the reversing part. The section from the reversing part 113 from the next reversing part is the spiral pitch. The planar optical fiber tape pertaining to the invention is accommodated in this slot 113 whose spiraling direction is periodically reverse to constitute an optical fiber cable. Such an optical fiber cable structure helps reduce the distortion of the optical fibers by the bending of the cable. The optical fiber tape pertaining to the invention constitutes such a slot type cable.

Figure 11:
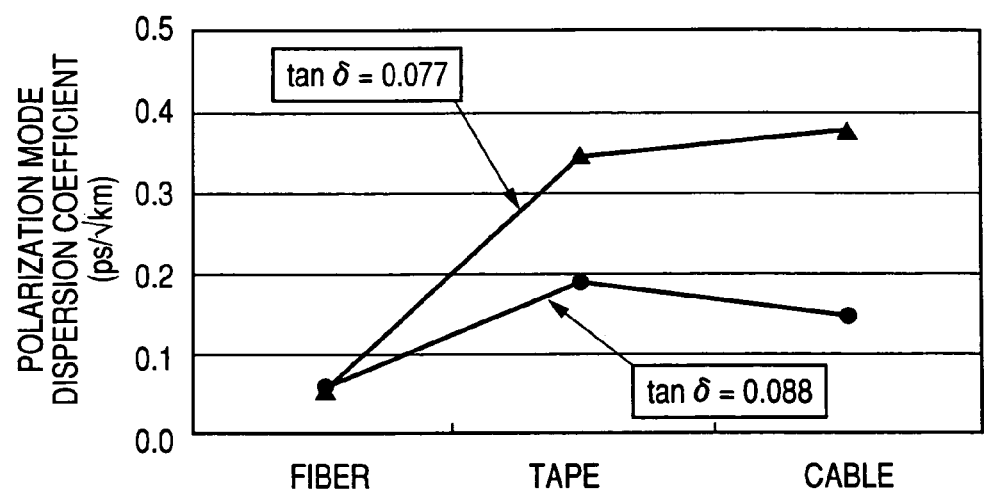
FIG. 11 is a diagram illustrating the polarization mode dispersion coefficients of two loss tangents in the state of optical fiber, that of tape and that of cable.

FIG. 11 illustrates the polarization mode dispersion (PMD) coefficients of two loss tangent in the state of fiber strand, that of tape core containing those fibers and that of SZ slot type cable containing that tape where dispersion shift optical fibers are used. Here are shown the case of the local maximum loss tangent of tan δ=0.088 in Example 2 and that of tan δ=0.077 in Example 3. Thus it is seen that, in order obtain satisfactory PMD characteristics in a state of cable as a transmission path, PMD characteristics in the state of tape is also important in addiction to PMD of fiber strands themselves.

As hitherto described, it has been found that the optical fiber tape according to the invention makes it possible to reduce the polarization mode dispersion coefficient where the loss tangent measured of the optical fiber tape is higher. Since this enables the spread of pulses at the time transmission to be restrained, it is made possible to supply optical fiber tapes suitable for high transmission speed of several Gb/s to several tens of Gb/s, a DWDM system of non-regenerative relay transmission for a long distance can be architected.

What is claimed:

1. An optical fiber tape integrating a plurality of optical fibers with a tape bonding material, characterized in that the local maximum level of the loss tangent in a state of optical fiber tape is not less than 0.042 so that the local maximum level of the polarization mode dispersion of any optical fiber in the optical fiber tape is not more than 0.3 ps/√km.

2. An optical fiber tape composed by arranging a plurality of resin-coated optical fibers in one lateral row and then using an ultraviolet curing resin around the optical fibers as the tape bonding material, characterized in that the local maximum level of the loss tangent in a state of optical fiber tape is not less than 0.042 so that the local maximum level of the polarization mode dispersion of any optical fiber in the optical fiber tape is not more than 0.3 ps/√km.

3. The optical fiber tape according to claim 1 or 2, wherein an ultraviolet curing resin is used as said tape bonding material, the ultraviolet curing resin consists of a photopolymerizing prepolymer, photopolymerizing monomer or a photopolymerization initiator, the photopolymerizing prepolymer consists of one or a combination of more of urethane acrylate resin, epoxy acrylate resin, polyol acrylate resin, butadiene acrylate resin, polyester acrylate resin and silicon acrylate resin, the photopolymerizing monomer consists of one or a combination of more of vinyl pyrrolidone, hydroxy ethyl acrylate and ethyihexyl acrylate, and the photopolymerization initiator consists of one or a combination of more of benzophenone compound, acryl phosphine oxide compound and acetophenone compound.

4. The optical fiber tape according to claim 1 or 2, characterized in that the local maximum level of the loss tangent in a state of optical fiber tape is not less than 0.050 and the local maximum level of the polarization mode dispersion of any optical fiber in the optical fiber tape is not more than 0.2 ps/√km.

5. The optical fiber tape according to claim 1 or 2, characterized in that single mode optical fibers are used as said optical fibers in the optical fiber tape.

6. The optical fiber tape according to claim 1 or 2, characterized in that dispersion shift optical fibers are used as the optical fibers in the optical fiber tape.

7. The optical fiber tape according to claim 1, characterized in that the local maximum level of the loss tangent in a state of optical fiber tape is not less than 0.080.

8. The optical fiber tape according to claim 1 or 2, characterized in that the local maximum level of the loss tangent in a state of optical fiber tape is not less than 0.085 and the local maximum level of the polarization mode dispersion of any optical fiber in the optical fiber tape is not more than 0.2 ps/$\sqrt{\text{km}}$.

9. The optical fiber tape core according to claim 7, characterized in that dispersion shift optical fibers are as said optical fibers in the optical fiber tape.

10. The optical fiber tape of claim 2, wherein the local maximum level of the polarization mode dispersion of any optical fiber in the optical fiber tape is not more than 0.3 ps/$\sqrt{\text{km}}$, wherein the local maximum level of the loss tangent in a state of optical fiber tape is not less than 0.080, and said optical fibers in the optical fiber tape comprise dispersion shift optical fibers.

11. An optical fiber assembly, comprising:
a plurality of optical fibers; and
an optical fiber tape disposed about said optical fibers and fixing said optical fibers with a tape bonding material, wherein a local maximum level of a polarization mode dispersion of any of said optical fibers being not more than 0.3 ps/$\sqrt{\text{km}}$ and a local maximum level of a loss tangent in a state of the optical fiber tape being not less than 0.042.

12. An optical fiber assembly, comprising:
a plurality of resin-coated optical fibers in a lateral row; and
an optical fiber tape disposed about said resin-coated optical fibers and including an ultraviolet curing resin that holds said resin-coated optical fibers, wherein
a local maximum level of a polarization mode dispersion of any of said resin-coated optical fibers being not more than 0.03 ps/$\sqrt{\text{km}}$, and
a local maximum level of a loss tangent in a state of the optical fiber tape being not less than 0.042.

* * * * *